(12) United States Patent
Yang et al.

(10) Patent No.: US 11,339,380 B2
(45) Date of Patent: May 24, 2022

(54) GLUTAMATE DEHYDROGENASE MUTANT AND APPLICATION THEREOF

(71) Applicant: ZHEJIANG UNIVERSITY, Zhejiang (CN)

(72) Inventors: Lirong Yang, Zhejiang (CN); Xinjian Yin, Zhejiang (CN); Jianping Wu, Zhejiang (CN); Gang Xu, Zhejiang (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 16/684,509

(22) Filed: Nov. 14, 2019

(65) Prior Publication Data

US 2020/0362317 A1    Nov. 19, 2020

(30) Foreign Application Priority Data

May 15, 2019 (CN) .......................... 201910403331.2

(51) Int. Cl.
 *C12N 9/04* (2006.01)
 *C12N 9/06* (2006.01)
 (Continued)

(52) U.S. Cl.
 CPC ........... *C12N 9/0016* (2013.01); *C12N 15/74* (2013.01); *C12P 13/001* (2013.01); *C12Y 104/01002* (2013.01)

(58) Field of Classification Search
 CPC .................................................. C12N 9/0016
 See application file for complete search history.

(56) References Cited

U.S. PATENT DOCUMENTS 4,265,654 A     5/1981   Takematsu et al.
10,865,391 B2 * 12/2020  Yang ............... C12Y 104/01004

FOREIGN PATENT DOCUMENTS

CN      106978453       7/2017

OTHER PUBLICATIONS

Studer. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — Jiwen Chen; Jacobson Holman PLLC (57) ABSTRACT

The invention discloses a glutamate dehydrogenase mutant and an application thereof. The mutant is one of the following: a mutant of the amino acid sequence of SEQ ID NO. 1 which has a mutation at lysine at position 402 to phenylalanine or aspartic acid; a mutant which has a mutation at isoleucine at position 406 to phenylalanine or threonine; a mutant which has a mutation at threonine at position 121 and leucine at position 123; a mutant which has a mutation at alanine at position 379 and leucine at position 383. In the invention, the catalytic activity of glutamate dehydrogenase derived from *Pseudomonas putida* to 2-carbonyl-4-(hydroxymethylphosphonoyl)butanoic acid (PPO) is significantly improved by a molecular transformation method combining directed evolution and a semi-rational design; and the issue of low glutamate dehydrogenase activity in the process of preparing L-glufosinate by reductive amination is solved.

6 Claims, 6 Drawing Sheets

Specification includes a Sequence Listing.

(51) Int. Cl.
*C12N 15/74* (2006.01)
*C12P 13/00* (2006.01)

(56) References Cited

OTHER PUBLICATIONS

Google translation of CN 106978453. retrived via patent.google.com on Feb. 23, 2021.*
R. C. Hudson et al., "L-Glutamate Dehydrogenases: Distribution, Properties and Mechanism", Comp. Biochem. Physiol., Dec. 1993, pp. 767-792.

* cited by examiner

SEQUENCE LISTING

<160> NUMBER OF SEQ ID NOS: 12

<210> SEQ ID NO 1
<211> LENGTH: 449
<212> TYPE: PRT
<213> ORGANISM: Unknown
<220> FEATURE:
<223> OTHER INFORMATION: Pseudomonas putida

<400> SEQUENCE: 1

```
Met Ser Thr Met Ile Glu Ser Val Asp Asn Phe Leu Ala Arg Leu Lys
1               5                   10                  15

Gln Arg Asp Pro Gly Gln Pro Glu Phe His Gln Ala Val Glu Val
            20                  25                  30

Leu Arg Thr Leu Trp Pro Phe Leu Glu Ala Asn Pro His Tyr Leu Gln
            35                  40                  45

Ser Gly Ile Leu Glu Arg Met Val Glu Pro Glu Arg Ala Val Leu Phe
        50                  55                  60

Arg Val Ser Trp Val Asp Asp Gln Gly Lys Val Gln Val Asn Arg Gly
65                  70                  75                  80

Tyr Arg Ile Gln Met Ser Ser Ala Ile Gly Pro Tyr Lys Gly Gly Leu
                85                  90                  95

Arg Phe His Pro Ser Val Asn Leu Ser Val Leu Lys Phe Leu Ala Phe
            100                 105                 110

Glu Gln Val Phe Lys Asn Ser Leu Thr Ser Leu Pro Met Gly Gly Gly
            115                 120                 125

Lys Gly Gly Ser Asp Phe Asp Pro Lys Gly Lys Ser Asp Ala Glu Val
        130                 135                 140

Met Arg Phe Cys Gln Ala Phe Met Ser Glu Leu Tyr Arg His Ile Gly
145                 150                 155                 160

Ala Asp Cys Asp Val Pro Ala Gly Asp Ile Gly Val Gly Ala Arg Glu
                165                 170                 175

Ile Gly Phe Met Phe Gly Gln Tyr Lys Arg Leu Ala Asn Gln Phe Thr
            180                 185                 190

Ser Val Leu Thr Gly Lys Gly Met Thr Tyr Gly Gly Ser Leu Ile Arg
            195                 200                 205

Pro Glu Ala Thr Gly Tyr Gly Cys Val Tyr Phe Ala Glu Glu Met Leu
        210                 215                 220

Lys Arg Gln Asp Lys Arg Ile Asp Gly Arg Arg Val Ala Val Ser Gly
225                 230                 235                 240

Ser Gly Asn Val Ala Gln Tyr Ala Ala Arg Lys Val Met Asp Leu Gly
                245                 250                 255

Gly Lys Val Ile Ser Leu Ser Asp Ser Glu Gly Thr Leu Tyr Ala Glu
            260                 265                 270

Ala Gly Leu Thr Asp Ala Gln Trp Asp Ala Leu Met Glu Leu Lys Asn
            275                 280                 285

Val Lys Arg Gly Arg Ile Ser Glu Leu Ala Gly Gln Phe Gly Leu Glu
        290                 295                 300

Phe Arg Lys Gly Gln Thr Pro Trp Ser Leu Pro Cys Asp Ile Ala Leu
305                 310                 315                 320

Pro Cys Ala Thr Gln Asn Glu Leu Gly Ala Glu Asp Ala Arg Thr Leu
                325                 330                 335

Leu Arg Asn Gly Cys Ile Cys Val Ala Glu Gly Ala Asn Met Pro Thr
            340                 345                 350

Thr Leu Glu Ala Val Asp Ile Phe Leu Asp Ala Gly Ile Leu Tyr Ala
```

```
            355                 360                 365
Pro Gly Lys Ala Ser Asn Ala Gly Gly Val Ala Val Ser Gly Leu Glu
        370                 375                 380
Met Ser Gln Asn Ala Met Arg Leu Leu Trp Thr Ala Gly Glu Val Asp
385                 390                 395                 400
Ser Lys Leu His Asn Ile Met Gln Ser Ile His Ala Cys Val His
                405                 410                 415
Tyr Gly Glu Glu Ala Asp Gly Arg Ile Asn Tyr Val Lys Gly Ala Asn
                420                 425                 430
Ile Ala Gly Phe Val Lys Val Ala Asp Ala Met Leu Ala Gln Gly Val
            435                 440                 445
Val

<210> SEQ ID NO 2
<211> LENGTH: 261
<212> TYPE: PRT
<213> ORGANISM: Unknown
<220> FEATURE:
<223> OTHER INFORMATION: Bacillus subtilis

<400> SEQUENCE: 2

Met Tyr Pro Asp Leu Lys Gly Lys Val Val Ala Ile Thr Gly Ala Ala
1               5                   10                  15
Ser Gly Leu Gly Lys Ala Met Ala Ile Arg Phe Gly Lys Glu Gln Ala
                20                  25                  30
Lys Val Val Ile Asn Tyr Tyr Ser Asn Lys Gln Asp Pro Asn Glu Val
                35                  40                  45
Lys Glu Glu Val Ile Lys Ala Gly Gly Glu Ala Val Val Val Gln Gly
            50                  55                  60
Asp Val Thr Lys Glu Glu Asp Val Lys Asn Ile Val Gln Thr Ala Ile
65                  70                  75                  80
Lys Glu Phe Gly Thr Leu Asp Ile Met Ile Asn Asn Ala Gly Leu Glu
                85                  90                  95
Asn Pro Val Pro Ser His Glu Met Pro Leu Lys Asp Trp Asp Lys Val
                100                 105                 110
Ile Gly Thr Asn Leu Thr Gly Ala Phe Leu Gly Ser Arg Glu Ala Ile
            115                 120                 125
Lys Tyr Phe Val Glu Asn Asp Ile Lys Gly Asn Val Ile Asn Met Ser
            130                 135                 140
Ser Val His Glu Val Ile Pro Trp Pro Leu Phe Val His Tyr Ala Ala
145                 150                 155                 160
Ser Lys Gly Gly Ile Lys Leu Met Thr Arg Thr Leu Ala Leu Glu Tyr
                165                 170                 175
Ala Pro Lys Gly Ile Arg Val Asn Asn Ile Gly Pro Gly Ala Ile Asn
                180                 185                 190
Thr Pro Ile Asn Ala Glu Lys Phe Ala Asp Pro Lys Gln Lys Ala Asp
            195                 200                 205
Val Glu Ser Met Ile Pro Met Gly Tyr Ile Gly Glu Pro Glu Glu Ile
        210                 215                 220
Ala Ala Val Ala Ala Trp Leu Ala Ser Lys Glu Ala Ser Tyr Val Thr
225                 230                 235                 240
Gly Ile Thr Leu Phe Ala Asp Gly Gly Met Thr Leu Tyr Pro Ser Phe
                245                 250                 255
Gln Ala Gly Arg Gly
            260
```

<210> SEQ ID NO 3
<211> LENGTH: 31
<212> TYPE: DNA
<213> ORGANISM: Artificial Sequence
<220> FEATURE:
<223> OTHER INFORMATION: Synthetic

<400> SEQUENCE: 3
cgcggatcca tgtctaccat gatcgaatct g                              31

<210> SEQ ID NO 4
<211> LENGTH: 29
<212> TYPE: DNA
<213> ORGANISM: Artificial Sequence
<220> FEATURE:
<223> OTHER INFORMATION: Synthetic

<400> SEQUENCE: 4
cccaagcttt cagaccacgc cctgagcca                                 29

<210> SEQ ID NO 5
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(10)
<223> OTHER INFORMATION: n is a, c, g, or t

<400> SEQUENCE: 5
tggacagcnn kctgcacaac atcatgcagt c                              31

<210> SEQ ID NO 6
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is a, c, g, or t

<400> SEQUENCE: 6
ttgtgcagmn ngctgtccac ttcaccggcc g                              31

<210> SEQ ID NO 7
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 7
tcgctgndtt cgndtcccat gggcggcggc aaggg                          35

<210> SEQ ID NO 8

```
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 8
catgggahnc gaahncagcg agttcttgaa cacct                           35

<210> SEQ ID NO 9
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 9
ggcgtandtg tgtcgggcnd tgaaatgtcg cagaacgcca t                    41

<210> SEQ ID NO 10
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 10
catttcahng cccgacacah ntacgccgcc cgcattggag g                    41

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
tgagatccgg ctgctaacaa a                                          21

<210> SEQ ID NO 12
<211> LENGTH: 21
<212> TYPE: DNA
<213> ORGANISM: Artificial Sequence
```

```
<220> FEATURE:
<223> OTHER INFORMATION: Synthetic

<400> SEQUENCE: 12
tttgttagca gccggatctc a                                              21
```

GLUTAMATE DEHYDROGENASE MUTANT AND APPLICATION THEREOF

CROSS-REFERENCE TO RELATED APPLICATION

This application claims the priority benefit of China application serial no. 201910403331.2, filed on May 15, 2019. The entirety of the above-mentioned patent application is hereby incorporated by reference herein and made a part of this specification.

BACKGROUND OF THE INVENTION

Field of the Invention

The invention relates to the technical field of enzyme engineering, in particular to a glutamate dehydrogenase mutant and an application thereof in the preparation of L-glufosinate by catalyzing 2-carbonyl-4-(hydroxymethylphosphonoyl)butanoic acid.

Description of Related Art

Phosphinothricin (also known as glufosinate) is a phosphorus-containing amino acid herbicide, chemically known as 2-amino-4-(hydroxymethylphosphonoyl)butanoic acid, the third largest herbicide in the world and the second largest genetically-modified crop herbicide. Glufosinate has the characteristics of wide herbicidal spectrum, low toxicity, high activity, partial conductivity, and good environmental compatibility and is widely used in weed removal of non-cultivated land, no-tillage land, farmland crops, aquatic fields, and the like. Among the two configurations of glufosinate, only the L-form has herbicidal activity (Herbicidal compositions [P]. Patent application U.S. Pat. No. 4,265,654 A, 1981), and is easily degraded in the soil and is less harmful to the environment.

At present, the market-selling glufosinate is a racemic mixture. If used in the pure optical isomer form of L-configuration, the application amount of glufosinate is reduced by 50%, which may significantly improve economy and reduce environment pressure. Therefore, the development of optically pure L-glufosinate preparation process is of great significance.

Glutamate dehydrogenase (EC 1.4.1.2-1.4.1.4) is rich in source and diverse in nature, and has great potential for application in the field of chiral L-amino acid synthesis (L-glutamate dehydrogenases: Distribution, properties and mechanism [J]. Comparative Biochemistry & Physiology B Comparative Biochemistry, 1993,106(4): 767-792.) Preparation of L-glufosinate by asymmetric reductive amination of 2-carbonyl-4-(hydroxymethylphosphonoyl)butanoic acid (PPO) catalyzed by glutamate dehydrogenase has significant advantages such as strict stereoselectivity, 100% theoretical yield, easy separation and purification of the product, and the like.

In the invention patent application publication No. CN106978453A, we cloned the glutamate dehydrogenase (PpGluDH, NCBI login number: NP_742836.1) gene derived from *Pseudomonas putida* and overexpressed it in *E. coli*. The recombinant glutamate dehydrogenase is capable of reductively aminating 2-carbonyl-4-(hydroxymethylphosphonoyl)butanoic acid to produce L-glufosinate having higher optical purity. However, from the viewpoint of industrial application, the catalytic activity of PpGluDH is low, which brings about a series of issues such as excessive catalyst preparation cost and post-treatment difficulty. Therefore, improving the catalytic activity of PpGluDH on PPO by molecular modification is the key to realize the industrial application of the L-glufosinate reductive amination synthesis process.

SUMMARY OF THE INVENTION

The invention aims at the issue that the glutamate dehydrogenase derived from *Pseudomonas putida* has low catalytic activity on the non-natural substrate 2-carbonyl-4-(hydroxymethylphosphonoyl)butanoic acid, and provides a plurality of glutamate dehydrogenase mutants with significantly improved enzyme activity and uses thereof in the synthesis of L-glufosinate.

The specific technical solutions are as follows:

The invention provides a glutamate dehydrogenase mutant. The glutamate dehydrogenase mutant is one of the following:

(1) a mutant of an amino acid sequence of SEQ ID NO. 1 which has a mutation at lysine at position 402 to phenylalanine or aspartic acid;

(2) a mutant of the amino acid sequence of SEQ ID NO. 1 which has a mutation at isoleucine at position 406 to phenylalanine or threonine;

(3) a mutant of the amino acid sequence of SEQ ID NO. 1 which has a mutation at threonine at position 121 and leucine at position 123 respectively to serine and histidine, or asparagine and tyrosine, or valine and tyrosine, or serine and serine, or asparagine and phenylalanine, or valine and phenylalanine, or isoleucine and tyrosine;

(4) a mutant of the amino acid sequence of SEQ ID NO. 1 which has a mutation at alanine at position 379 and leucine at position 383 respectively to isoleucine and tyrosine, or isoleucine and cysteine, or serine and tyrosine, or valine and serine, or phenylalanine and cysteine, or tyrosine and cysteine, or cysteine and cysteine.

In the invention, an error-prone PCR technique is used to introduce a random mutation into a glutamate dehydrogenase gene (Genebank ID: 1044501) derived from *Pseudomonas putida* to construct a random mutation library, and then the mutation library is screened by a high-throughput screening method. The enzyme activity of the resulting positive mutant strain is rescreened by an HPLC method. Mutant strains with improved PPO catalytic activity obtained by rescreening are analyzed for specific mutations by sequencing analysis.

The mutation situation of the positive mutants is obtained based on directed evolution, and three mutation libraries are designed and constructed, including a 402nd saturated mutation library, a 121st and 123rd combined mutation library, and the 379th and 383rd combined mutation library. The three mutation libraries are screened by a high-throughput screening technique, and the enzyme activity of the positive mutant strains obtained are rescreened by an HPLC method. Specific mutations of the mutant strains with improved PPO catalytic activity obtained by the rescreening are analyzed by sequencing.

The invention also provides an encoding gene of the glutamate dehydrogenase mutant.

The invention also provides an expression vector and engineered bacteria containing the glutamate dehydrogenase mutant encoding gene.

The invention also provides an application of the glutamate dehydrogenase mutant for preparing L-glufosinate by catalyzing 2-carbonyl-4-(hydroxymethylphosphonoyl)butanoic acid or a salt thereof.

The invention also provides a method for preparing L-glufosinate by catalyzing 2-carbonyl-4-(hydroxymethylphosphonoyl)butanoic acid or a salt thereof, including the following steps.

(1) A genetically-engineered bacteria expressing a glutamate dehydrogenase mutant is prepared, wherein the glutamate dehydrogenase mutant is as described in claim 1;

(2) the genetically-engineered bacteria is cultured to prepare an enzyme solution;

(3) the enzyme solution is added to a mixed system containing a substrate 2-carbonyl-4-(hydroxymethylphosphonoyl)butanoic acid, an amino donor, and a reduced coenzyme, and a reductive amination reaction is performed to obtain L-glufosinate.

In step (2), the enzyme solution is a resting cell suspension or a lysing crude enzyme solution of the genetically-engineered bacteria; of course, the pure enzyme obtained by purifying the crude enzyme solution is also applicable to the preparation method of the L-glufosinate of the invention.

Preferably, in step (3), the temperature of the reductive amination reaction is 15° C. to 50° C., and the pH of the reaction solution is 6 to 10.

In step (3), the reduced coenzyme is reduced nicotinamide adenine dinucleotide phosphate (NADPH).

Preferably, the reaction system of step (3) further includes a coenzyme regeneration system; the coenzyme regeneration system is a coenzyme regeneration system that uses glucose dehydrogenase as a coenzyme regenerating enzyme and glucose as a coenzyme regeneration substrate.

More preferably, in the reaction system in step (3), the glucose dehydrogenase gene (BsGDH-2M) is derived from *Bacillus subtilis*, and the stability thereof is improved by molecular transformation, and the encoded amino acid sequence thereof is SEQ ID NO. 2.

Further, in step (3), the amino donor is ammonium sulfate.

Compared with the prior art, the invention has the following beneficial effects:

In the invention, the catalytic activity of the glutamate dehydrogenase derived from *Pseudomonas putida* to 2-carbonyl-4-(hydroxymethylphosphonoyl))butanoic acid (PPO) is significantly improved by a molecular transformation method combining directed evolution with a semi-rational design. The invention solves the issue of low glutamate dehydrogenase activity in the process of preparing L-glufosinate by reductive amination. The catalytic activity of the glutamate dehydrogenase mutant of the invention on PPO is significantly improved, and the enzyme activity of the unit fermentation broth is up to 11.21 U/mL, which is 102 times that of the wild-type. The glutamate dehydrogenase mutant of the invention exhibits good catalytic efficiency in the preparation of L-glufosinate, the substrate conversion rate is >99%, and the L-glufosinate concentration is up to 80.6 g/L, and the ee value >99%, which shows very large industrial application prospects. The invention successfully solves the key issue of low biocatalyst activity in the process of preparing L-glufosinate by amination reduction reaction, and lays a foundation for realizing the industrial application of the process.

BRIEF DESCRIPTION OF THE DRAWINGS

The accompanying drawings are included to provide a further understanding of the invention, and are incorporated in and constitute a part of this specification. The drawings illustrate embodiments of the invention, and together with the description, serve to explain the principles of the invention.

In particular, A is a $^1$H NMR spectrum of PPO; and B is a $^{13}$C NMR spectrum of PPO.

DESCRIPTION OF THE EMBODIMENTS

The invention is further described below in conjunction with specific embodiments. It is to be understood that the following embodiments are merely illustrative of the invention and are not intended to limit the scope of the invention.

The experimental methods in the invention are conventional methods unless otherwise specified, and the specifics of gene cloning operation are as provided in "Molecular Cloning Experiment Guide" by J. Sambrook et al.

Reagents for upstream genetic engineering operations: DNA polymerase (EasyTaq DNA Polymerase) for error-prone PCR in Example 1 of the invention was purchased from Beijing TransGen Biotech; in Example 2 of the invention, DNA polymerase (PrimeSTAR® Max DNA Polymerase) and Dpn I were purchased from TaKaRa (Dalian) Co., Ltd.; ClonExpress II One Step Cloning Kit was purchased from Nanjing Vazyme Biotech Co., Ltd.; the plasmid extraction kit was purchased from Axygen Hangzhou Co., Ltd.; *E. coli* BL21 (DE3), plasmid, etc. were purchased from Novagen; and primer synthesis and gene sequencing were completed by Hangzhou TsingKe Biological technology Co., Ltd. Refer to the product manual for the use of the above reagents.

The recombinant *E. coli* carrying the glutamate dehydrogenase gene of the invention is constructed and deposited by our laboratory. The vector used was pET-28a(+) and the host used was *E. coli* BL21 (DE3).

Figure 2:
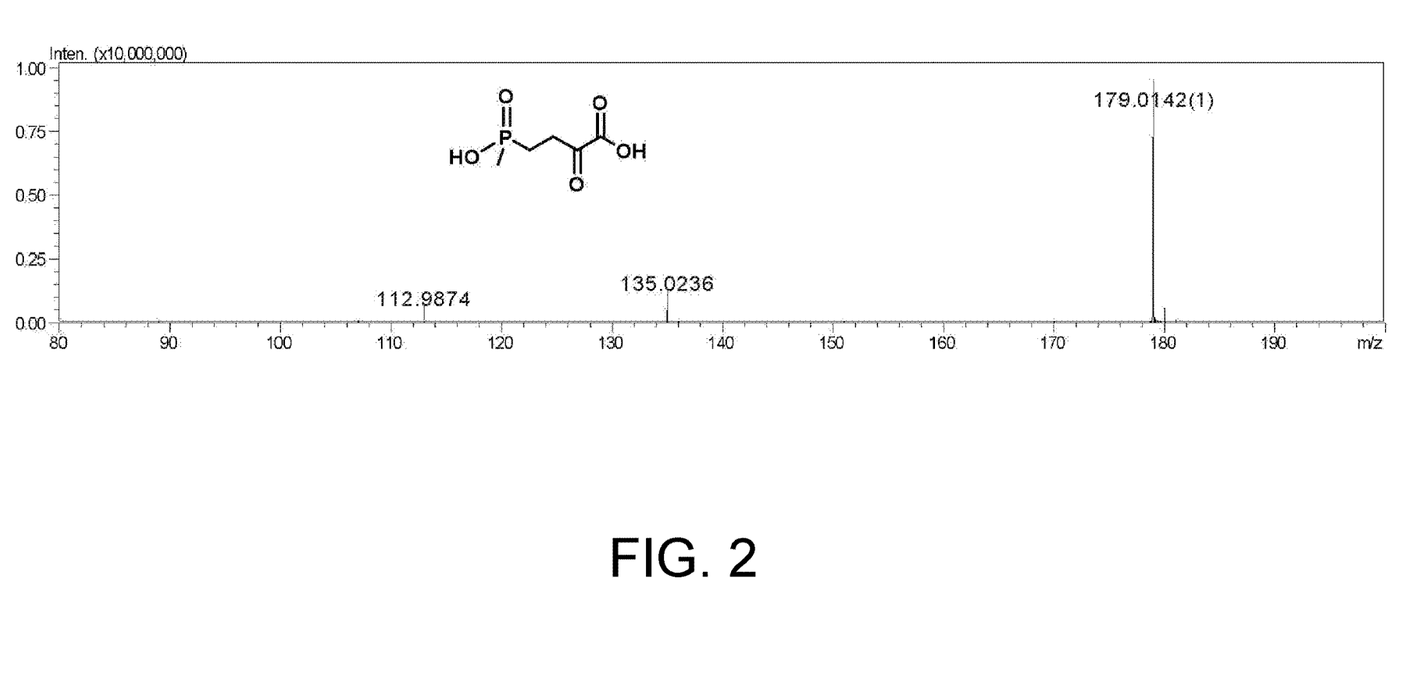
FIG. 2 is a mass spectrum of the starting material 2-carbonyl-4-(hydroxymethylphosphonoyl)butanoic acid (abbreviated as PPO).
Figure 3:
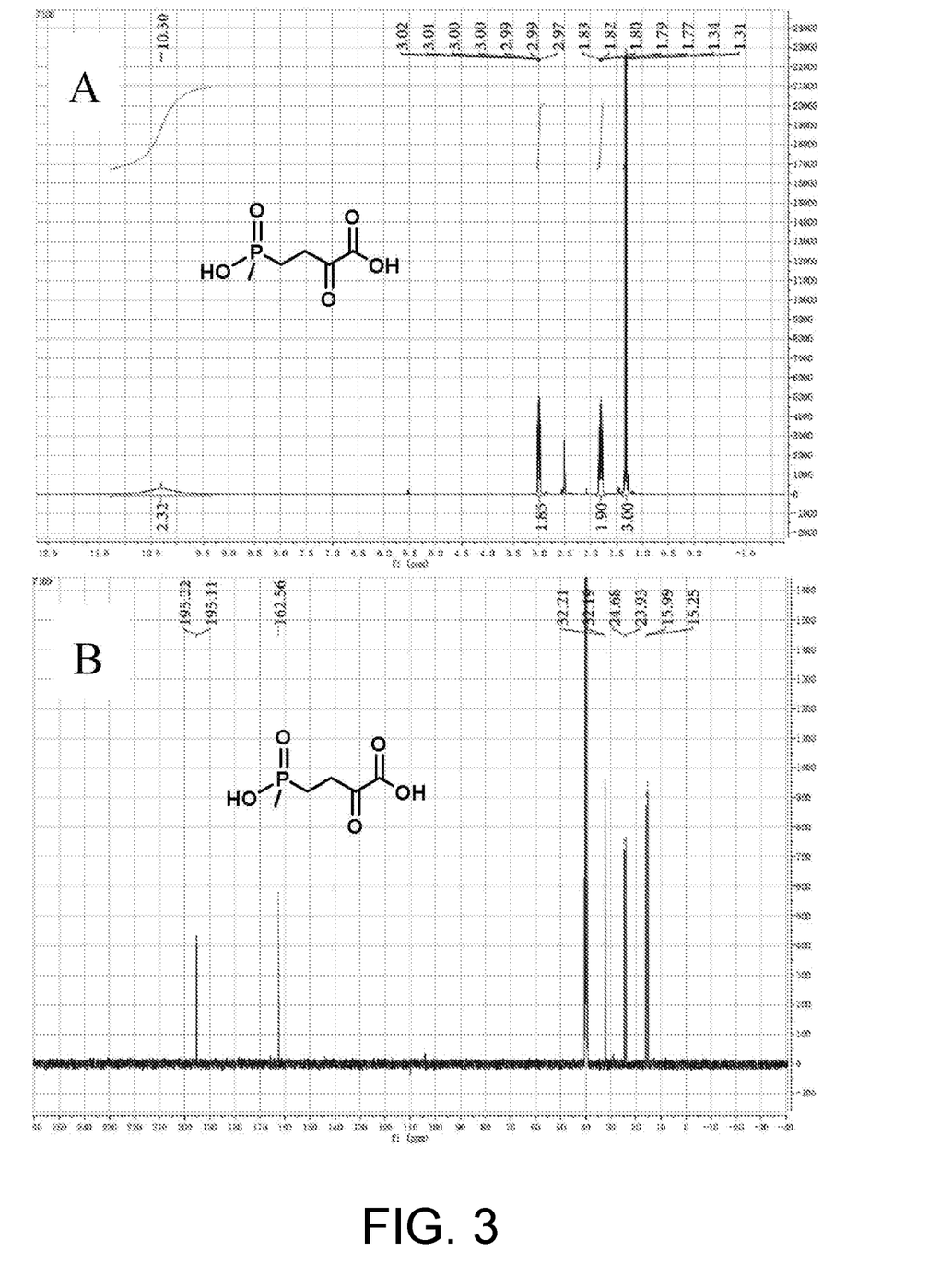
FIG. 3 is a nuclear magnetic diagram of the starting material 2-carbonyl-4-(hydroxymethylphosphonoyl)butanoic acid (PPO).

The reagent used in the downstream catalytic process: 2-carbonyl-4-(hydroxymethylphosphonoyl)butanoic acid (abbreviated as PPO) was artificially synthesized, and the mass spectrum and nuclear magnetic diagram thereof are shown in FIGS. 2 and 3; DL-glufosinate standard was purchased from Sigma-Aldrich; NADP$^+$ and NADPH were purchased from Bontac-Bio-Engineering (Shenzhen) Co., Ltd.; other commonly used reagents were purchased from Sinopharm Chemical Reagent Co., Ltd. The three-letter or one-letter expression of the amino acids used in the specification of the present application adopted the amino acid code specified by IUPAC (Eur. J. Biochem., 138:9-37,1984).

Glutamate dehydrogenase enzyme standard assay system: appropriate amount of enzyme solution, 100 mM substrate, 10 mM NADPH, 500 mM NH$_4^+$ ((NH$_4$)$_2$SO$_4$), total system was 400 µL, reaction medium was pH 7.5 0.1 M phosphoric acid salt buffer. The reaction was performed at 35° C. for 10 minutes, and the reaction was ended by the addition of 40 uL of 5 M NaOH. The L-glufosinate concentration produced in the sample was quantified by pre-column derivatization HPLC.

Definition of enzyme unit (U): the amount of enzyme required to produce 1 μmol of L-glufosinate per minute under standard reaction conditions.

Figure 4:
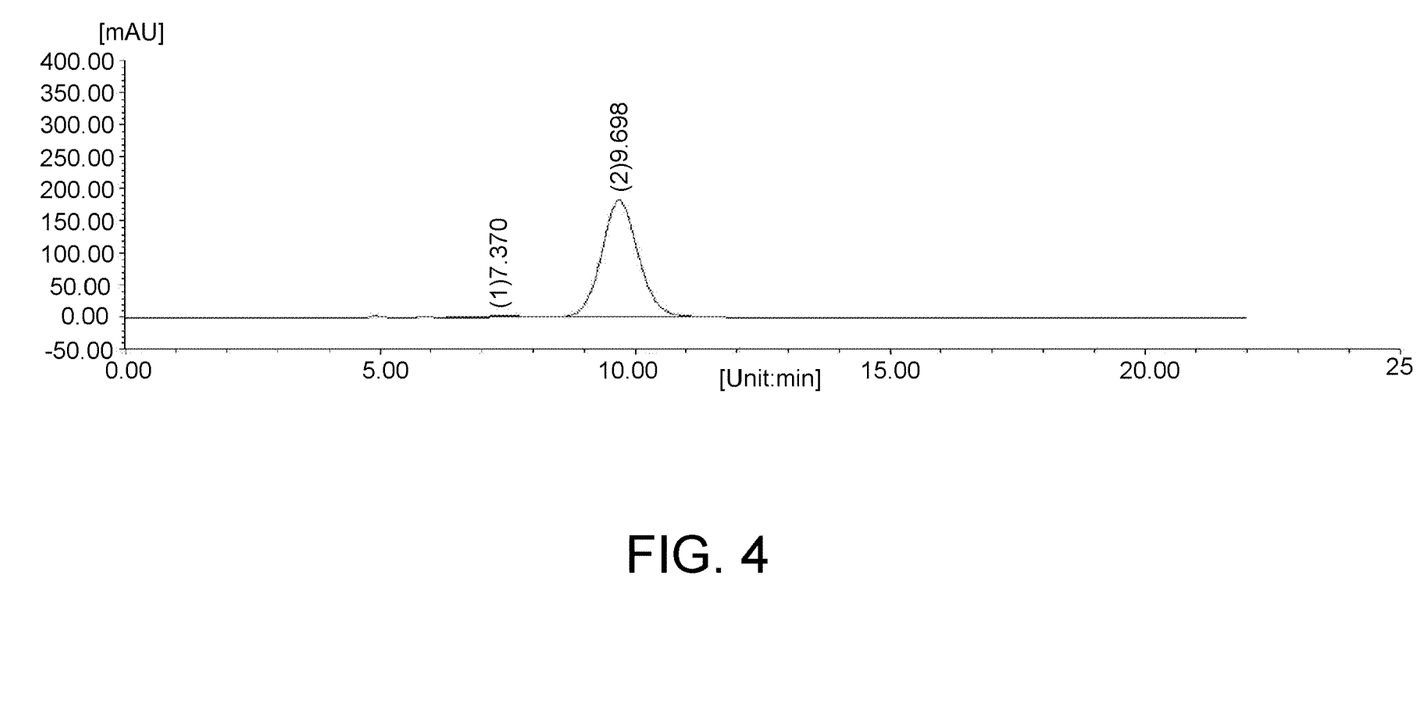
FIG. 4 is a standard high-performance liquid detection spectrum of the substrate 2-carbonyl-4-(hydroxymethylphosphonoyl)butanoic acid (non-chiral analysis, 5 mM); wherein the retention time of the substrate PPO is 9.7 minutes.

In the invention, the progress of the reaction was monitored by analyzing the concentration of the substrate in the reaction solution by high-performance liquid chromatography (HPLC). HPLC analysis method: column model: Pntulips® QS-C18, 5 μm, 4.6 mm×250 mm. Mobile phase: 50 mM $(NH_4)_2HPO_4$, 1% of 10% tetrabutylammonium hydroxide aqueous solution was added, pH was adjusted to 3.6 with 50% phosphoric acid (mass fraction), and 8% acetonitrile was added. Detection wavelength: 205 nm. Flow rate: 1.0 mL/min. Column temperature: 40° C. See FIG. 4 for the peak of the substrate.

The chiral analysis and concentration analysis of L-glufosinate were performed by pre-column derivatization HPLC. The specific analysis method was:

(1) Chromatographic conditions: column model: Pntulips® QS-C18, 5 μm, 4.6 mm×250 mm. Mobile phase: 50 mM sodium acetate solution: acetonitrile=8:0.5. Detection wavelength: 338 nm. Flow rate: 0.85 mL/min. Column temperature: 30° C.

(2) Derivatization reagent: 0.03 g of o-phthalaldehyde and 0.1 g of N-acetam-L-cysteine were weighed separately, solubilized with 400 uL of ethanol, and then 4 mL of 0.2 mol/L boric acid buffer (pH 9.8) was added, then oscillated for complete dissolution, and then stored in a refrigerator at 4° C. as reserve (for no more than 4 days).

(3) Derivatization reaction and determination: 100 μL of sample was added to 150 μL of derivatization reagent, mixed and kept at 25° C. for 5 minutes. 1 mL of pure water was added for dilution, filmed, and 20 uL was sampled for analysis.

Figure 5:
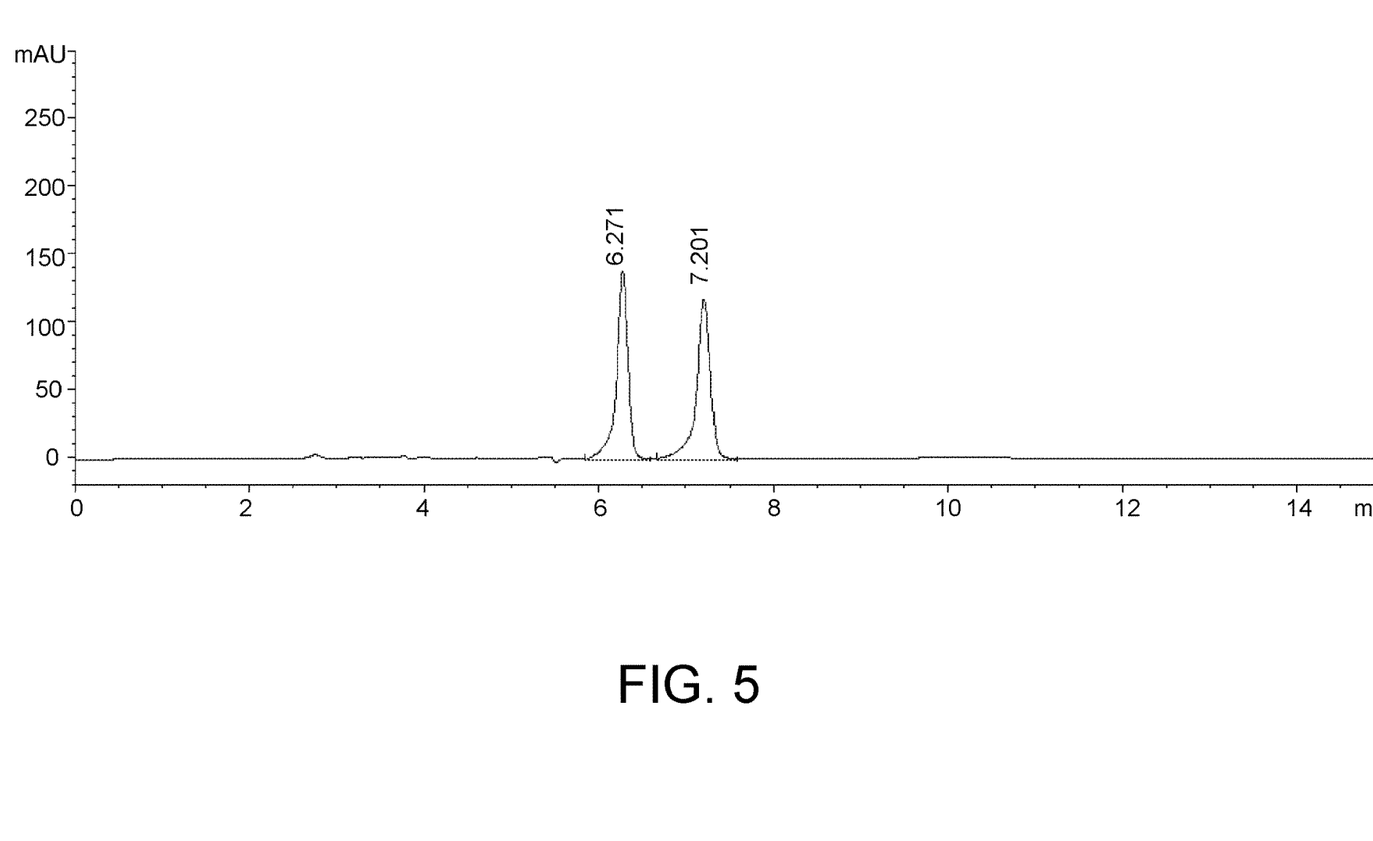
FIG. 5 is an HPLC of the standard pre-column derivatization of racemic phosphinothricin (chiral analysis, 2 mM); wherein the retention time is 6.3 minutes for L-glufosinate and 7.2 minutes for D-glufosinate.

The peak of D-glufosinate and L-glufosinate is shown in FIG. 5.

EXAMPLE 1

*Pseudomonas putida*-Derived Glutamate Dehydrogenase (PpGluDH) Directed Evolution Based on Error-Prone PCR Step 1: Activation of PpGluDH Recombinant Strain and Plasmid Extraction

*E. coli*-engineered bacteria carrying pET-28a(+)-PpGluDH recombinant plasmid were activated and cultured using LB medium.

The specific formula of LB was is: peptone 10 g/L, yeast powder 5 g/L, NaCl 10 g/L, dissolved in deionized water then kept at constant volume, sterilized at 121° C. for 20 minutes, and kept ready for use. The solid medium was LB medium supplemented with 2% agar.

A glycerol tube containing a PpGluDH recombinant strain was streaked onto a dish containing LB solid medium (50 μg/mL kanamycin), and cultured in static at 37° C. for 12 hours. A single colony was picked from the dish and placed in 5 mL of LB medium containing 50 μg/mL kanamycin, and cultured at 37° C., 200 rpm for 12 hours. After the culture solution was obtained, the plasmid was extracted according to the instruction manual of the plasmid extraction kit.

Step 2: Construction of Random Mutation Library

The pET-28a(+)-PpGluDH plasmid extracted in step 1 was used as a template, and a random mutation was introduced into the PpGluDH gene by error-prone PCR. The primers and PCR reaction systems used are shown in Table 1 and Table 2, respectively.

TABLE 1

| Primers for error-prone PCR | |
| --- | --- |
| Primer | Sequence (5' to 3')[a] |
| PpGluDH-F | CGCG<u>GATCC</u>ATGTCTACCATGATCGAATCTG (BamHI) |
| PpGluDH-R | CCC<u>AAGCTT</u>TCAGACCACGCCCTGAGCCA (HindIII) |

Note:
[a]restriction endonuclease sites were respectively added to the upstream and downstream primers, as shown by the underline, and the specific restriction endonuclease is shown in the parentheses in the primer sequence.

TABLE 2

| PCR amplification system | |
| --- | --- |
| Component | Volume (uL) |
| EasyTaq DNA Polymerase | 1 |
| PpGluDH-F (10 uM) | 1.5 |
| PpGluDH-R (10 uM) | 1.5 |
| 10 × EasyTaq buffer | 5 |
| dNTPs (2.5 mM) | 4 |
| Plasmid template | 1 |
| $Mn^{2+}$ solution (5 mM) | 8 |
| $ddH_2O$ | 28 |

Error-prone PCR amplification conditions:
1) pre-denaturation at 94° C. for 3 minutes;
2) denaturation at 94° C. for 30 seconds, annealing at 58° C. for 30 seconds, extension at 72° C. for 2 minutes (cycle 35 times in this phase);
3) post-extension at 72° C. for 8 minutes;
4) storage at 4° C.

After the end of PCR amplification, the amplified product was detected by 1.0% agarose gel electrophoresis, and the target band was purified and recovered by a DNA recovery and purification kit. The recovered PCR amplified product and the expression vector pET-28a(+) were respectively double digested with the corresponding restriction endonucleases at 37° C. for 3 hours. The enzyme digestion system is shown in the following table:

TABLE 3

| Enzyme digestion system | |
| --- | --- |
| Reagent | Volume (μL) |
| PCR amplification product/plasmid | 15 |
| BamHI | 2 |
| HindIII | 2 |
| dd $H_2O$ | 17 |
| 10 × Buffer | 4 |

After the enzyme digestion, the digested product was purified and recovered by using a DNA purification kit. The digested PCR amplified product was ligated to the expression vector pET-28a(+) with the corresponding nick using T4 DNA ligase, and the ligation system is shown in the following table:

TABLE 4

Enzyme system

| Reagent | Volume (μL) |
| --- | --- |
| PCR amplification product | 10 |
| Vector | 7 |
| T4 ligase | 1 |
| 10 × ligase buffer | 2 |

The enzyme-linked product was transformed into *E. coli* BL21 (DE3) competent cells, plated, and placed in an inverted culture at 37° C. until a single colony of appropriate size was grown.

Step 3: High-Throughput Screening of Random Mutation Libraries-Primary Screening 200 μL of LB medium (50 μg/mL kanamycin) was added to a sterilized 96-deep well plate and a single colony was picked to the 96-deep well plate using a sterile tip. The deep well plate was then placed at 37° C. and cultured at 200 rpm for 8 hours and referred to as the primary plate. 400 μL of LB medium (50 μg/mL kanamycin) was added to an additional sterilized 96-well plate as a secondary plate. 50 μL of the bacterial solution was pipetted into the secondary plate in the primary plate, and 20% glycerin was added to the primary plate and placed in a refrigerator at −80° C. for long-term storage. The secondary plate was then oscillated and cultured at 37° C. for 3 hours, induced by IPTG at a final concentration of 0.5 mM, and then the secondary plate was placed at 18° C. and cultured at 200 rpm for 18 hours.

The secondary plate was centrifuged at 4000 rpm at 4° C. for 20 minutes to collect the bacteria, and then frozen at −80° C. for 3 hours or more. The secondary plate was removed from −80° C. and allowed to thaw at room temperature for 0.5 hours. Then, 300 μL of lysate (10 mM pH 7.5 phosphate buffer, 750 mg/L lysozyme, 10 mg/L DNase I) was added to each well, and the cells were suspended by oscillation and placed in a shaker at 37° C. and incubated at 200 rpm for 1 hour. After the incubation, the cells were centrifuged at 4000 rpm at 4° C. for 20 minutes, and the supernatant was taken for enzyme activity measurement.

An assay mixture for screening was prepared: pH 7.5 phosphate buffer (0.1 M), 2 mM NADPH, 20 mM substrate PPO, 1 M $NH_4^+$. 200 μL of the assay mixture was added to each well of a fresh 96-well plate (reaction plate) and kept at 37° C. for 15 minutes. 200 μL of enzyme solution was pipetted into the reaction plate to start the reaction. 100 uL was sampled at 20 minutes, 40 minutes, and 60 minutes, respectively and added to an enzyme plate pre-charged with 100 uL of pH 7.5 phosphate buffer (0.1 M), and the absorbance at 340 nm was measured using a microplate reader. The lower the absorbance, the higher the catalytic activity, and the selection of a mutant strain with an absorbance significantly lower than that of the control (wild-type) was used as a candidate strain for rescreening.

Step 4: Rescreening

The mutants exhibiting a significant increase in enzyme activity in the primary screening were subjected to rescreening by HPLC. After the corresponding mutant strains on the primary plate were activated by dish scribing, a single colony was inoculated into 5 mL LB liquid medium containing 50 μg/mL kanamycin and oscillated and cultured at 37° C. for 12 hours. 2% of the inoculum was transferred to 50 mL of LB liquid medium also containing 50 μg/mL kanamycin, and when $OD_{600}$ reached around 0.6 to 0.8 by oscillation and culturing at 37° C., IPTG was added to reach a final concentration of 0.5 mM, and then the inoculum was inductively cultured at 18° C. for 16 hours. After the completion of the culture, 12,000 g of the culture solution was centrifuged at 4° C. for 10 minutes, and the supernatant was discarded to collect the bacteria. The bacteria collected after the completion of the culture were washed twice with 50 mM of pH 7.5 phosphate buffer, resuspended in the pH 7.5 phosphate buffer, and ultrasonically disrupted 30 times at 400 W, with each ultrasound lasting 3 seconds and pausing 7 seconds. The cell-disrupted solution was centrifuged at 12,000 g at 4° C. for 10 minutes to remove the precipitate, and the obtained supernatant was a crude enzyme solution.

Figure 1:
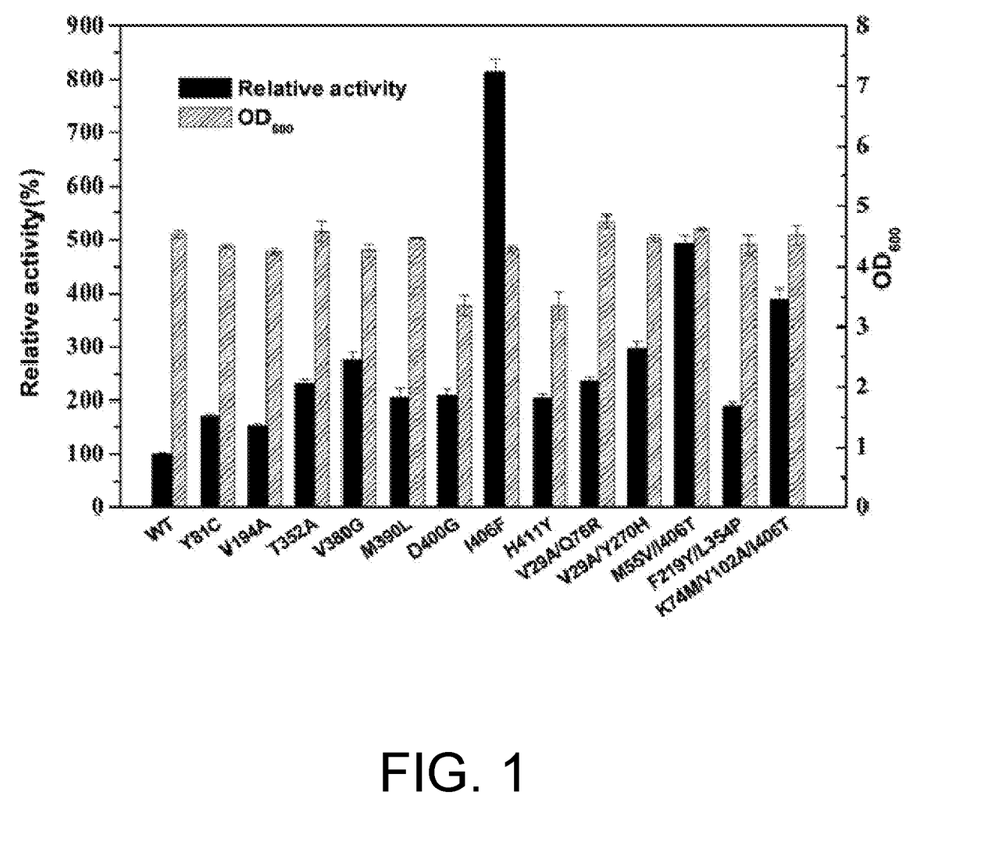
FIG. 1 shows the results of measuring wild-type and mutant activities of PpGluDH in Example 1.

The crude enzyme activity of PPO was determined for each mutant strain according to the standard enzyme activity assay system. Lastly, 13 mutants with significantly improved enzyme activity were obtained, containing 8 single-point mutant strains, 4 two-point mutant strains, and 1 three-point mutant strain. The enzyme activity of the unit volume fermentation broth was 0.167 U/mL to 0.897 U/mL, which was 1.5 to 8.2 times that of the original glutamate dehydrogenase. See FIG. 1 for details. Mutations in the two-point and three-point mutant strains that were positively mutated were analyzed by reverse mutation, and the positive mutations in these mutant strains were determined to be the three mutations of V29A, L354P, and I406T. A summary of the positive mutations obtained by directed evolution of PpGluDH is shown in Table 5.

TABLE 5

Summary of positive mutations obtained by directed evolution

| Site | Codon mutation (before mutation → after mutation) | Amino acid mutation (before mutation → after mutation) | Mutant strain enzyme activity (U/mL) | Enzyme activity increase factor[a] |
| --- | --- | --- | --- | --- |
| 29 | GTG→GCA | Val→Ala | 0.252 ± 0.013 | 2.3 |
| 81 | TAC→TGC | Tyr→Cys | 0.188 ± 0.004 | 1.7 |
| 194 | GTG→GCG | Val→Ala | 0.167 ± 0.006 | 1.5 |
| 352 | ACT→GCT | Thr→Ala | 0.255 ± 0.009 | 2.3 |
| 354 | GTC→CCC | Leu→Pro | 0.315 ± 0.011 | 2.9 |
| 380 | GTG→GGG | Val→Gly | 0.303 ± 0.018 | 2.8 |
| 390 | ATG→TTG | Met→Leu | 0.226 ± 0.021 | 2.1 |
| 400 | GAC→GGC | Asp→Gly | 0.230 ± 0.015 | 2.1 |
| 406 | ATC→ACC | Ile→Thr | 0.613 ± 0.019 | 5.6 |
| 406 | ATC→TTC | Ile→Phe | 0.897 ± 0.026 | 8.2 |
| 411 | CAC→TAC | His→Tyr | 0.223 ± 0.102 | 2.0 |

Note:
[a] fold-increase in the enzyme activity of the mutant strain relative to the PpGluDH wild-type (0.11 U/mL)

EXAMPLE 2

Construction and Screening of Focus Saturated Mutation Library

The results of Example 1 were analyzed to perform saturated mutation on the 121th, 123th, 379th, 383th, and 402th amino acid residues of PpGluDH. Primers (Table 6) were designed, and pET-28a(+)-PpGluDH plasmid was used as a template and K402X-F, T121X/L123X-F, or A379X/L383X-F and Aid-R were used as primer pairs to obtain linearized short fragments, and then PCR was performed using K402X-R, T121X/L123X-R, or A379X/L383X-R and Aid-F as primer pairs to obtain linearized long fragments. The user manual of ClonExpress II One Step Cloning Kit was used for subsequent Dpn I digestion, gel recovery, recombination, and transformation operations to construct the three mutation libraries of a 402nd saturated mutation library (K402X), a 121st and 123rd combined mutation library (T121X/L123X), and a 379th and 383rd combined mutation library (A379X/L383X).

TABLE 6

Primers used to construct a focused saturated mutation library

| Primer | Sequence (5' to 3') |
|---|---|
| K402X-F | TGGACAGCNNKCTGCACAACA TCATGCAGTC |
| K402X-R | TTGTGCAGMNNGCTGTCCACT TCACCGGCCG |
| T121X/L123X-F | TCGCTGNDTTCGNDTCCCATG GCGGCGGCAAGGG |
| T121X/L123X-R | CATGGGAHNCGAAHNCAGCGA GTTCTTGAACACCT |
| A379X/L383X-F | GGCGTANDTGTGTCGGCNDT GAAATGTCGCAGAACGCCAT |
| A379X/L383X-R | CATTTCAHNGCCCGACACAHN TACGCCGCCCGCATTGGAGG |
| Aid-F | TGAGATCCGGCTGCTAACAAA |
| Aid-R | TTTGTTAGCAGCCGGATCTCA |

The three mutation libraries were pre-screened by the high-throughput screening method described in Example 1, and then subjected to rescreening by HPLC. Lastly, two mutant strains with significant increase in PPO enzyme activity were obtained from the 402nd saturated mutation library (K402X): K402F and K402D; seven mutant strains with significant increase in PPO enzyme activity were screened from the 121st and 123rd combined mutation library (T121X/L123X): T121S/L123H, T121N/L123Y, T121V/L123Y, T121S/L123S, T121N/L123F, T121V/L123F, T121I/L123Y; and seven mutant strains with significant increase in PPO enzyme activity were screened from the 379th and 383rd combined mutation library (A379X/L383X): A379I/L383Y, A379I/L383C, A379S/L383Y, A379V/L383S, A379F/L383C, A379Y/L383C, A379C/L383C. The specific mutations and changes in enzyme activity are shown in Table 7.

TABLE 7

Screening results of mutation library

| Mutation library | Site | Raw amino acid | Mutated amino acid | Mutant strain enzyme activity (U/mL) | Enzyme activity increase factor[a] |
|---|---|---|---|---|---|
| K402X | 402 | Lys | Phe; | 0.42 ± 0.03 | 3.8 |
| | | | Asp | 0.21 ± 0.01 | 1.9 |
| T121X/L123X | 121/123 | Thr/Leu | Ser/His | 5.42 ± 0.26 | 49.3 |
| | | | Asn/Tyr | 11.21 ± 0.57 | 102 |
| | | | Val/Tyr | 3.71 ± 0.50 | 33.7 |
| | | | Ser/Ser | 2.79 ± 0.09 | 25.4 |
| | | | Asn/Phe | 2.59 ± 0.19 | 23.5 |
| | | | Val/Phe | 2.02 ± 0.16 | 18.4 |
| | | | Ile/Tyr | 2.00 ± 0.23 | 18.2 |
| A379X/L383X | 379/383 | Ala/Leu | Ile/Tyr | 1.01 ± 0.02 | 9.2 |
| | | | Ile/Cys | 2.11 ± 0.05 | 19.2 |
| | | | Ser/Tyr | 0.61 ± 0.04 | 5.5 |
| | | | Val/Ser | 1.63 ± 0.01 | 14.8 |
| | | | Phe/Cys | 1.94 ± 0.10 | 17.6 |
| | | | Tyr/Cys | 1.52 ± 0.07 | 13.8 |
| | | | Cys/Cys | 2.25 ± 0.10 | 20.5 |

Note:
[a]fold-increase in the enzyme activity of the mutant strain relative to the PpGluDH wild-type (0.11 U/mL)

EXAMPLE 3

Preparation of L-Glufosinate by Glutamic Acid Dehydrogenase Wild-Type (PpGluDH) and Glucose Dehydrogenase Double Enzyme Coupling Culture of bacteria and preparation of crude enzyme solution: glycerol tubes of engineered bacteria harboring wild-type PpGluDH and glucose dehydrogenase (BsGDH-2M, SEQ ID NO. 2) were activated by dish scribing, and then a single colony was inoculated in 50 mL LB liquid medium containing 50 μg/mL kanamycin and oscillated and cultured at 37° C. for 12 hours. 2% of the inoculum was transferred to 1 L of fresh LB liquid medium also containing 50 μg/mL kanamycin, and when $OD_{600}$ reached around 0.6 by oscillation and culturing at 37° C., IPTG was added to reach a final concentration of 0.5 mM, and then the inoculum was inductively cultured at 18° C. for 16 hours. After the completion of the culture, the culture solution was centrifuged at 12000 g at 4° C. for 10 minutes, the bacteria was collected, and a crude enzyme solution was prepared by ultrasonic disruption.

The reaction system was 30 mL containing 500 mM substrate PPO, 600 mM glucose, 250 mM $(NH_4)_2SO_4$, and 0.5 mM $NADP^+$. The concentration of glutamate dehydrogenase (dry weight) was 1.25 g/L, and the concentration of glucose dehydrogenase (dry weight) was 1.25 g/L. The reaction temperature was controlled at 35° C. by a water bath, and the pH was controlled at 7.5 by dropwise addition of aqueous ammonia. After 12 hours of reaction, the residual concentration of PPO was detected by achiral HPLC, and the amount of L-glufosinate produced and the ee value thereof were determined by pre-column derivatization HPLC.

The reaction end data is as follows: PPO had 373 mM remaining, and the conversion rate was 25.4%. The production concentration of L-glufosinate was 20.5 g/L, and the ee value >99%.

EXAMPLE 4

Glutamate Dehydrogenase Mutant Strain (PpGluDH-T121N/L123Y), Glucose Dehydrogenase Double Enzyme Coupling for Preparation of L-Glufosinate An engineered bacteria expressing glutamate dehydrogenase (PpGluDH-T121N/L123Y) and glucose dehydrogenase (BsGDH-2M, SEQ ID NO. 2) was cultured in the same manner as in Example 3, and the cells were collected by centrifugation and disrupted by ultrasound to prepare a crude enzyme solution.

The reaction system was 30 mL containing 500 mM substrate PPO, 600 mM glucose, 250 mM $(NH_4)_2SO_4$, and 0.5 mM $NADP^+$. The concentration of glutamate dehydrogenase (dry weight) was 1.25 g/L, and the concentration of glucose dehydrogenase (dry weight) was 1.25 g/L. The reaction temperature was controlled at 35° C. by a water bath, and the pH was controlled at 7.5 by dropwise addition of aqueous ammonia. After 2.5 hours of reaction, the residual concentration of PPO was detected by achiral HPLC, and the amount of L-glufosinate produced and the ee value thereof were determined by pre-column derivatization HPLC.

Figure 6:
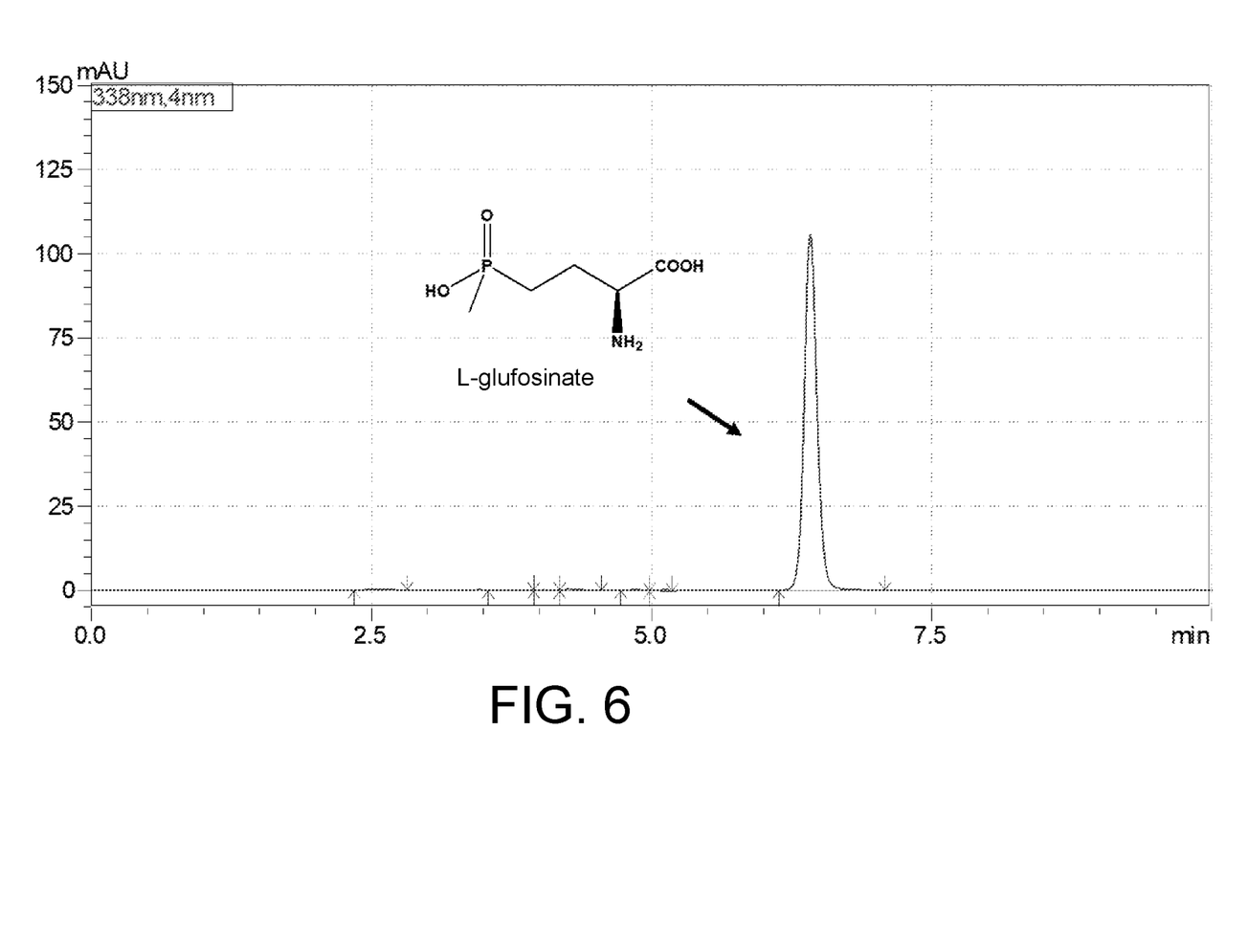
FIG. 6 is a pre-column derivatization high-performance liquid detection spectrum (chiral analysis) of the reaction solution (upon completion of the reaction) in Example 4.

The reaction end data is as follows: PPO had 2.4 mM remaining, and the conversion rate was 99.5%. The production concentration of L-glufosinate was 80.6 g/L, and the ee value >99% (FIG. 6).

EXAMPLE 5

Glutamate Dehydrogenase Mutant Strain (PpGluDH-A379C/L383C), Glucose Dehydrogenase Double Enzyme Coupling for Preparation of L-Glufosinate An engineered bacteria expressing glutamate dehydrogenase (PpGluDH-A379C/L383C) and glucose dehydrogenase (BsGDH-2M, SEQ ID NO. 2) was cultured in the same manner as in Example 3, and the cells were collected by centrifugation and disrupted by ultrasound to prepare a crude enzyme solution.

The reaction system was 30 mL containing 500 mM substrate PPO, 600 mM glucose, 250 mM $(NH_4)_2SO_4$, and 0.5 mM $NADP^+$. The concentration of glutamate dehydrogenase (dry weight) was 1.25 g/L, and the concentration of glucose dehydrogenase (dry weight) was 1.25 g/L. The reaction temperature was controlled at 35° C. by a water bath, and the pH was controlled at 7.5 by dropwise addition of aqueous ammonia. After 5 hours of reaction, the residual concentration of PPO was detected by achiral HPLC, and the amount of L-glufosinate produced and the ee value thereof were determined by pre-column derivatization HPLC.

The reaction end data is as follows: PPO had 3.4 mM remaining, and the conversion rate was 99.3%. The production concentration of L-glufosinate was 79.4 g/L, and the ee value >99%.

EXAMPLE 6

Glutamate Dehydrogenase Mutant Strain (PpGluDH-I406F), Glucose Dehydrogenase Double Enzyme Coupling for Preparation of L-Glufosinate An engineered bacteria expressing glutamate dehydrogenase (PpGluDH-I406F) and glucose dehydrogenase (BsGDH-2M, SEQ ID NO. 2) was cultured in the same manner as in Example 3, and the cells were collected by centrifugation and disrupted by ultrasound to prepare a crude enzyme solution.

The reaction system was 30 mL containing 500 mM substrate PPO, 600 mM glucose, 250 mM $(NH_4)_2SO_4$, and 0.5 mM $NADP^+$. The concentration of glutamate dehydrogenase (dry weight) was 1.25 g/L, and the concentration of glucose dehydrogenase (dry weight) was 1.25 g/L. The reaction temperature was controlled at 35° C. by a water bath, and the pH was controlled at 7.5 by dropwise addition of aqueous ammonia. After 10 hours of reaction, the residual concentration of PPO was detected by achiral HPLC, and the amount of L-glufosinate produced and the ee value thereof were determined by pre-column derivatization HPLC.

The reaction end data is as follows: PPO had 4.6 mM remaining, and the conversion rate was 99.1%. The production concentration of L-glufosinate was 78.7 g/L, and the ee value >99%.

EXAMPLE 7

Glutamate Dehydrogenase Mutant Strain (PpGluDH-K402F), Glucose Dehydrogenase Double Enzyme Coupling for Preparation of L-Glufosinate An engineered bacteria expressing glutamate dehydrogenase (PpGluDH-K402F) and glucose dehydrogenase (BsGDH-2M, SEQ ID NO. 2) was cultured in the same manner as in Example 3, and the cells were collected by centrifugation and disrupted by ultrasound to prepare a crude enzyme solution.

The reaction system was 30 mL containing 500 mM substrate PPO, 600 mM glucose, 250 mM $(NH_4)_2SO_4$, and 0.5 mM $NADP^+$. The concentration of glutamate dehydrogenase (dry weight) was 1.25 g/L, and the concentration of glucose dehydrogenase (dry weight) was 1.25 g/L. The reaction temperature was controlled at 35° C. by a water bath, and the pH was controlled at 7.5 by dropwise addition of aqueous ammonia. After 12 hours of reaction, the residual concentration of PPO was detected by achiral HPLC, and the amount of L-glufosinate produced and the ee value thereof were determined by pre-column derivatization HPLC.

The reaction end data is as follows: PPO had 37.6 mM remaining, and the conversion rate was 92.5%. The production concentration of L-glufosinate was 72.8 g/L, and the ee value >99%.

What is claimed is:

1. A method for preparing L-glufosinate by catalyzing 2-carbonyl-4-(hydroxymethylphosphonoyl)butanoic acid or a salt thereof, comprising:
   (1) preparing a genetically-engineered bacteria expressing a glutamate dehydrogenase mutant, wherein the genetically-engineered bacteria is *E. coli*;
   (2) culturing the genetically-engineered bacteria to prepare an enzyme solution;
   (3) adding the enzyme solution to a system containing a substrate 2-carbonyl-4-(hydroxymethylphosphonoyl) butanoic acid, an amino donor, and a reduced coenzyme and performing a reductive amination reaction to obtain L-glufosinate,
   wherein the glutamate dehydrogenase mutant is one of the following:
   (a) the amino acid sequence of SEQ ID NO. 1 except for having a mutation of lysine at position 402 to phenylalanine or aspartic acid;
   (b) the amino acid sequence of SEQ ID NO. 1 except for having a mutation of threonine at position 121 and leucine at position 123 respectively to serine and histidine, or asparagine and tyrosine, or valine and tyrosine, or serine and serine, or asparagine and phenylalanine, or valine and phenylalanine, or isoleucine and tyrosine;
   (c) the amino acid sequence of SEQ ID NO. 1 except for having a mutation of alanine at position 379 and leucine at position 383 respectively to isoleucine and tyrosine, or isoleucine and cysteine, or serine and tyrosine, or valine and serine, or phenylalanine and cysteine, or tyrosine and cysteine, or cysteine and cysteine.

2. The method for preparing L-glufosinate by catalyzing 2-carbonyl-4-(hydroxymethylphosphonoyl)butanoic acid or a salt thereof of claim 1, wherein in step (3), a temperature of the reductive amination reaction is 15° C. to 50° C., and a pH of the reaction solution is 6 to 10.

3. The method for preparing L-glufosinate by catalyzing 2-carbonyl-4-(hydroxymethylphosphonoyl)butanoic acid or a salt thereof of claim 1, wherein in step (3), the reduced coenzyme is NADPH.

4. The method for preparing L-glufosinate by catalyzing 2-carbonyl-4-(hydroxymethylphosphonoyl)butanoic acid or a salt thereof of claim 1, wherein the reaction system of step (3) further comprises a coenzyme regeneration system; and the coenzyme regeneration system is a coenzyme regeneration system that uses glucose dehydrogenase as a coenzyme regenerating enzyme and glucose as a coenzyme regeneration substrate.

5. The method for preparing L-glufosinate by catalyzing 2-carbonyl-4-(hydroxymethylphosphonoyl)butanoic acid or a salt thereof of claim 4, wherein the amino acid sequence of the glucose dehydrogenase is SEQ ID NO. 2.

6. The method for preparing L-glufosinate by catalyzing 2-carbonyl-4-(hydroxymethylphosphonoyl)butanoic acid or a salt thereof of claim 1, wherein in step (3), the amino donor is ammonium sulfate.

* * * * *